United States Patent [19]
Wilk

[11] Patent Number: 5,284,162
[45] Date of Patent: Feb. 8, 1994

[54] METHOD OF TREATING THE COLON

[76] Inventor: Peter J. Wilk, 185 West End Ave., New York, N.Y. 10023

[21] Appl. No.: 913,442

[22] Filed: Jul. 14, 1992

[51] Int. Cl.⁵ .............................................. A61B 17/00
[52] U.S. Cl. .................................... 128/898; 606/205
[58] Field of Search .............. 606/140, 141, 205, 206; 128/898

[56] References Cited

U.S. PATENT DOCUMENTS

| | | | |
|---|---|---|---|
| 2,670,519 | 3/1954 | Recklitis | 606/206 |
| 4,374,523 | 2/1983 | Yoon | 606/140 |
| 4,393,872 | 7/1983 | Reznik et al. | 606/206 |
| 4,957,499 | 9/1990 | Lipatov et al. | 604/153 |
| 5,217,030 | 6/1993 | Yoon | 128/898 |

Primary Examiner—Jerome L. Kruter
Attorney, Agent, or Firm—R. Neil Sudol; Henry D. Coleman

[57] ABSTRACT

A surgical instrument assembly and method particularly for grasping and displacing a large tubular organ such as a colonic section during a laparoscopic procedure comprises an elongate rigid tubular member, an elongate rod having at least a portion slidably inserted in the tubular member, and two or four prongs connected to the rod at a distal end thereof. The prongs each have an arcuate configuration when ejected from a distal end of the tubular member by a distally directed motion of the rod. Upon ejection, the prongs form a substantially C-shaped clamping member with a pair of grasping jaws. The prongs are flattened out and pressed towards one another when the distal end of the tubular member is shifted over a proximal portion of the prongs.

13 Claims, 2 Drawing Sheets

METHOD OF TREATING THE COLON

BACKGROUND OF THE INVENTION

This invention relates to a surgical instrument assembly and an associated surgical technique.

During the performance of laparoscopic operations, it is frequently necessary to move an organ such as an intestine or an artery in order to reach an underlying organ. Such large tubular organs cannot be easily manipulated in laparoscopic surgery. Existing instruments such as grasping forceps have operating tips (e.g., jaws) which are basically too small to grasp a colon or major artery and move the organ without injury thereto.

OBJECTS OF THE INVENTION

An object of the present invention is to provide a surgical instrument or instrument assembly which may be used to grasp a relatively large internal organ of a patient such as the colon or the aorta.

A more particular object of the present invention is to provide such a surgical instrument or instrument assembly which may be used to partially shift larger internal organs of a patient.

Another, related object of the present invention is to provide such a surgical instrument or instrument assembly which may be used in laparoscopic surgery to grasp and partially shift a relatively large internal organ of a patient such as the colon or the aorta.

An associated object of the present invention is to provide a surgical technique which may be used to grasp, clamp and optionally shift a large internal organ of a patient such as the colon or the aorta, particularly in laparoscopic surgery but not exclusively limited thereto.

These and other objects of the present inventions will be apparent from the following descriptions and the drawings.

SUMMARY OF THE INVENTION

A surgical instrument assembly comprises, in accordance with the present invention, an elongate tubular member, an elongate rod having at least a portion slidably inserted in the tubular member, and two prongs connected to the rod at a distal end thereof. The prongs each have an arcuate configuration when ejected from a distal end of the tubular member by a distally directed motion of the rod. Upon ejection, the prongs form a pair of grasping jaws. The prongs are flattened out and pressed towards one another when retracted into the distal end of the tubular member by a proximally directed motion of the rod or, alternatively, when the tubular member is pushed in the distal direction over proximal end portions of the prongs.

Pursuant to a particular feature of the present invention, each of the prongs has a flattened transverse cross-section with rounded edges.

Pursuant to another particular feature of the present invention, each of the prongs is one of a pair of prongs, whereby the rod is provided at a distal end with two pairs of jaws.

A surgical instrument assembly comprises, in accordance with another conceptualization of the present invention, an elongate member provided at a distal end with a generally C-shaped clamping member having a pair of opposed arcuate arms. The instrument assembly further comprises a closure device associated with and at least partially coextensive with the elongate member in a longitudinal direction for pressing the arms towards one another to partially flatten the arms, thereby closing the clamping member about an object.

According to another feature of the present invention, the arms are integral with the elongate member and with one another, the arms being made of a resilient material having a limited degree of flexibility and an internal spring force whereby the arms are maintained in an opened configuration in the absence of a closure force.

According to a further feature of the present invention, the closure device includes a tubular member surrounding at least a portion of the elongate member. The tubular member cooperates with the arms in a camming action to press the arms towards one another upon relative motion of the tubular member and the arms towards each other.

According to additional features of the present invention, the elongate member is a rod slidably inserted into the tubular member, while each of the arms has a flattened transverse cross-section with rounded edges. Moreover, each of the arms may be one of a pair of arms, whereby the elongate member is provided at a distal end with two pairs of jaws.

A surgical method comprises, in accordance with the present invention, the steps of (a) inserting a distal end of an elongate tubular member into a patient's abdomen, (b) ejecting from a distal end of the tubular member a pair of prongs, (c) spreading the prongs apart from one another to form a pair of jaws during the step of ejecting, (d) moving the jaws towards an internal organ of the patient to insert a portion of the organ between the jaws, and (e) shifting the tubular member towards the prongs, thereby partially closing the jaws about the organ.

Accordingly, a large internal organ such as a colonic section or a portion of the aorta may be grasped and clamped in a method in accordance with the present invention. In the event of a traumatized or perforated organ such as the colon, the organ may be temporarily clamped on opposite sides of the perforation to prevent the spilling of fecal material into the abdomen, possibly infecting other organs. The perforation may then be repaired or patched.

In an optional step in accordance with the present invention, the organ is displaced relative to other organic tissues of the patient by exerting a force on the tubular member and the jaws. This displacement enables a surgeon to reach underlying tissues which would otherwise be difficult to access.

Where the prongs are connected to an elongate rod member slidably inserted into the tubular member, the step of ejecting includes the step of pushing the rod member in a distal direction through the tubular member.

Where the prongs are integral with one another and made of a resilient material having a limited degree of flexibility, the prongs may be collapsed towards one another by being drawn into the distal end of the tubular member. Also, the step of spreading includes the step of automatically spreading the prongs under the action of internal stresses.

The insertion of the tubular member into the patient's abdomen is accomplished by inserting the tubular member through a trocar sleeve which is disposed in the abdominal wall of the patient. Accordingly, the method is part of a laparoscopic procedure.

A surgical method comprises, in accordance with a further conceptualization of the present invention, the steps of (i) inserting a distal end of an elongate member into a patient's abdomen, (ii) subsequently opening a pair of opposed arcuate arms of a C-shaped clamping member connected to the elongate member at a distal end thereof, thereby forming a pair of jaws, (iii) moving the jaws towards an internal organ of the patient to insert a portion of the organ between the jaws, and (iv) pressing the arms towards one another to partially flatten the arms, thereby closing the clamping member about the organ.

In an optional step in accordance with the present invention, the organ is displaced relative to other organic tissues of the patient by exerting a force on the tubular member and the jaws. This displacement enables a surgeon to reach underlying tissues which would otherwise be difficult to access.

As discussed above, the arms are preferably integral with the elongate member and with one another and are made of a resilient material having a limited degree of flexibility and an internal spring force whereby the arms are maintained in an opened configuration in the absence of a closure force.

Pursuant to another feature of the present invention, the step of pressing includes the step of shifting an elongate tubular member towards the jaws to engage the jaws in a camming action and to partially close the jaws in opposition to the internal spring force.

Again, the insertion of the tubular member into the patient's abdomen is accomplished by inserting the tubular member through a trocar sleeve which is disposed in the abdominal wall of the patient. Accordingly, the method is part of a laparoscopic procedure.

A surgical instrument or instrument assembly in accordance with the present invention may be used to grasp and partially shift larger internal organs of a patient such as the colon or the aorta. The instrument assembly may be used in laparoscopic procedures, thereby substantially facilitating the procedure in certain cases. The instrument assembly may also be used as a clamp. For example, where an organ such as the colon is perforated, a pair of instrument assemblies in accordance with the invention may be used to temporarily clamp the colon on opposite sides of the perforation prior to a surgical closure of the perforation.

DETAILED DESCRIPTION

Figure 1:
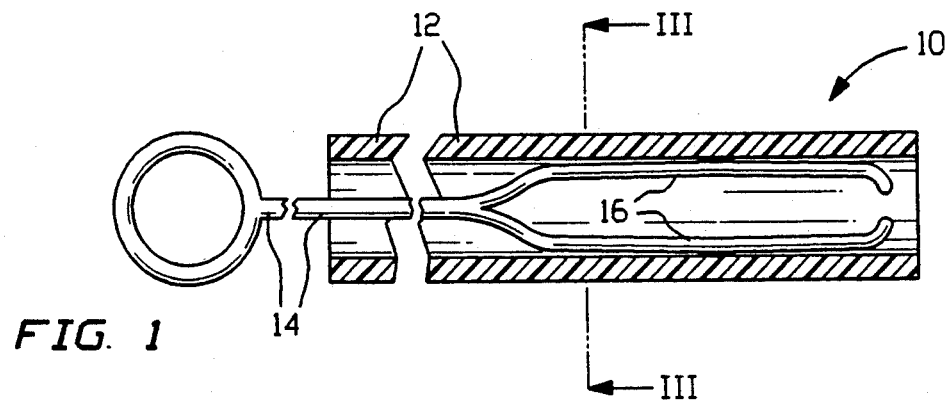
FIG. 1 is a partial longitudinal cross-sectional view of an instrument assembly in accordance with the present invention, showing a grasping or clamping member with a pair of prongs or arms in a collapsed or closed configuration in the distal end of a tubular member.
Figure 2:
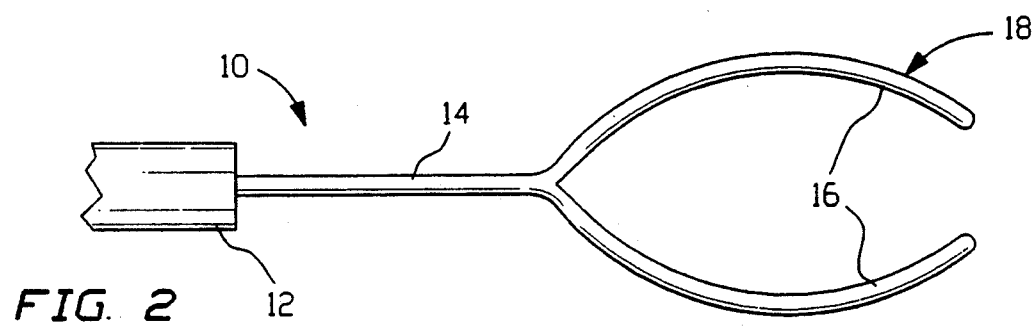
FIG. 2 is a schematic side elevational view of the instrument assembly of FIG. 1, showing the grasping or clamping member with the prongs or arms in an expanded or opened configuration outside the distal end of the tubular member.

As illustrated in FIGS. 1 and 2, a surgical instrument assembly 10 particularly utilizable in laparoscopic procedures for grasping and temporarily displacing large internal organs such as a colonic section comprises an elongate essentially rigid tubular member 12 and an elongate substantially rigid rod 14 slidably inserted in the tubular member. Two prongs or arms 16 are connected to rod 14 at a distal end thereof for forming jaws of a substantially C-shaped clamping or grasping member 18 upon an ejection of the prongs from the distal end of tubular member 12 by a distally directed stroke of rod 14.

Figure 6:
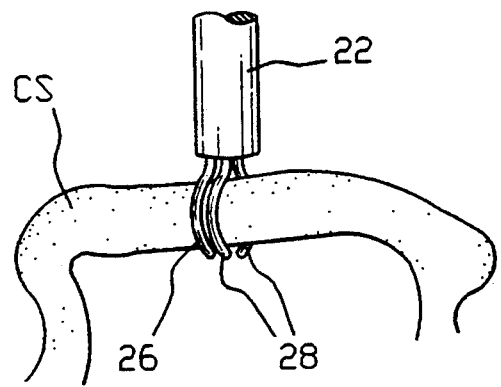
FIG. 6 is a schematic perspective view showing a subsequent step in using the instrument assembly of FIG. 4 to grasp a portion of a colon in a laparoscopic procedure.

Prongs 16 are integral With rod 14 and with one another and are formed with an internal spring force tending to maintain the prongs in an opened or expanded configuration (FIG. 2) in the absence of a closure force. Prongs 16 are made of a resilient material having a memory, i.e., a limited degree of flexibility, allowing a loading of the prongs into the distal end of tubular member 12 in a collapsed configuration (FIG. 1), subsequent expansion (FIG. 2), and partial closure during use of the instrument assembly to grasp and temporarily displace a colonic section or other large internal organ (FIG. 6).

The closure force for partially closing prongs or jaws 16 is supplied by tubular member 12. Tubular member 12 cooperates with prongs 16 in a camming action to press the prongs towards one another upon relative motion of the tubular member and the prongs towards each other.

Figure 3:
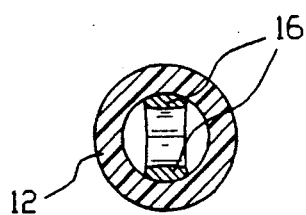
FIG. 3 is a cross-sectional view taken along line III—III in FIG. 1.

As illustrated in FIG. 3, each prong 16 has a flattened transverse cross-section with rounded edges.

Figure 4:
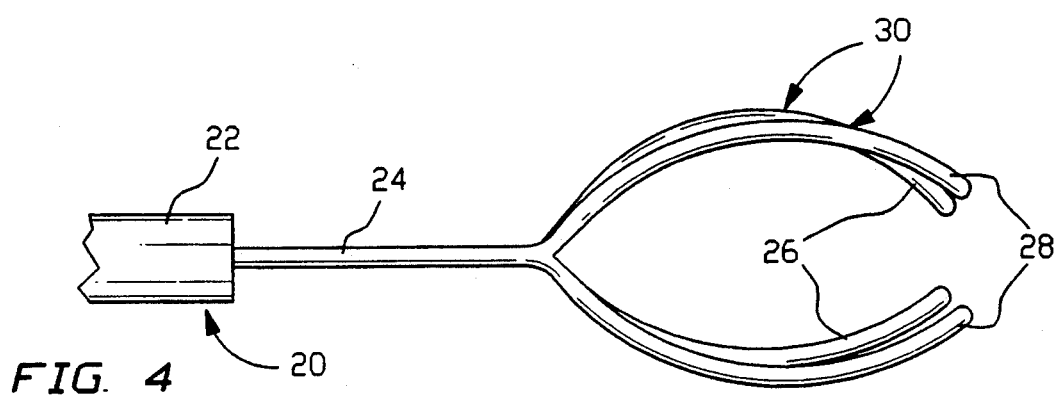
FIG. 4 is a schematic side elevational view of a modified instrument assembly, showing a grasping or clamping member with two pairs of prongs or arms in an expanded or opened configuration outside the distal end of a tubular member.

In the alternative embodiment of FIG. 4, a modified surgical grasper assembly 20 particularly utilizable in laparoscopic procedures for grasping and temporarily displacing large internal organs such as a colonic section includes an elongate essentially rigid tubular member 22 and an elongate substantially rigid rod 24 slidably inserted in the tubular member. Two pairs of prongs or arms 26 and 28 are connected to rod 24 at a distal end thereof for forming jaws of two substantially C-shaped clamping or grasping members 30 upon an ejection of the prongs from the distal end of tubular member 22 by a distally directed stroke of rod 24.

Prong 26 and 28 are integral with rod 24 and with one another and are formed with an internal spring force tending to maintain the prongs in an opened or expanded configuration in the absence of a closure force. Prongs 26 and 28 consist of a resilient material having a memory which allows an alternate collapsinq of the prongs into the forward end of tubular member 22 and an expanding of the prongs into an expanded configuration.

The closure force for partially closing prongs or jaws 26 and 28 is provided by tubular member 22. Tubular member 22 cooperates with prongs 26 and 28 in a camming action to press the prongs towards one another upon relative motion of the tubular member and the prongs towards each other.

Prongs 16, 26 and 28 each have an arcuate configuration when ejected from a distal end of the respective tubular member 12, 22 by a distally directed motion of rod 14, 24. Prongs 16, 26 and 28 are flattened out and pressed towards one another when retracted into the distal end of tubular member 12, 22 by a proximally directed motion of rod 14, 24 or, alternatively, when tubular member 12, 22 is pushed in the distal direction over proximal end portions of the prongs.

Prongs 26 and 28 likewise have have a flattened transverse cross-section with rounded edges, as described hereinabove for prongs 16 with reference to FIG. 3. The flattened cross-section maximizes tissue contact area. The rounded edges serve to eliminate any inadvertant cutting of an organ which is being grasped and shifted by the instrument assembly.

Figure 5:
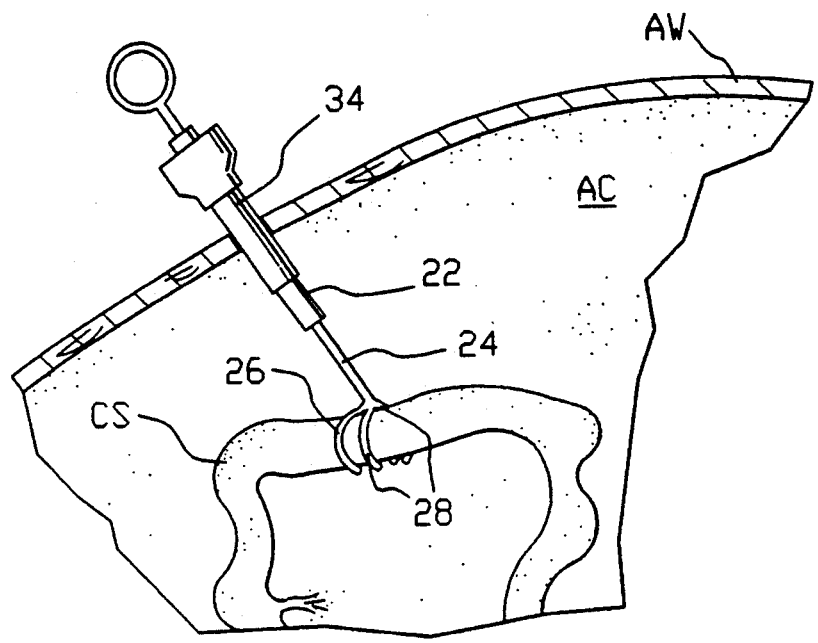
FIG. 5 is a schematic perspective view showing a step in using the instrument assembly of FIG. 4 to grasp a portion of a colon in a laparoscopic procedure.

As depicted in FIG. 5, a distal end of tubular member 12 or 22 is inserted into a patient's abdominal cavity AC through a trocar sleeve 34 which has been positioned in the abdominal wall AW. During this insertion step, prongs 16 or 26 and 28 are disposed in the distal end portion of the respective tubular member 12, 22. Upon insertion of tubular member 12 or 22 so that the distal end thereof protrudes into the abdominal cavity AC, rod 14 or 24 is pushed in the distal direction through tubular member 12, 22 to eject prongs 16 or 26, 28 from the tubular member. Prongs 16 or 26, 28 are spread apart under the action of their own internal spring forces to form a pair of generally C-shaped grasping and clamping jaws. The instrument assembly is then manipulated to move the jaws or prongs 16 or 26, 28 towards an internal organ such as colonic section CS to insert a portion of the organ between the jaws. Tubular member 12, 22 is then shifted towards prongs 16 or 26, 28, as illustrated in FIG. 6, to cam against the prongs and thereby partially close the jaws or prongs 16, or 26, 28 about the colonic section CS. Section CS may then be displaced relative to other organic tissues of the patient by exerting a force on jaws or prongs 16 or 26, 28 via tubular member 12, 22 and rod 14, 24.

After the laparoscopic procedure utilizing the instrument assembly, tubular member 12, 22 is pulled in a proximal direction relative to rod 14, 24 to enable an opening of prongs 16, 26, 28 under the action of their own internal spring forces. Upon a manipulation of the instrument assembly to remove the colonic section CS from the grasping and clamping jaws, prongs 16, 26, 28 are then collapsed by pulling on rod 14, 24 relative to tubular member 12, 22 to draw the prongs back into the distal end of the tubular member.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that surgical instrument assemblies in accordance with the present invention may be utilized in operations other than laparoscopic surgery. Even in open abdominal surgery, it is frequently necessary to move an organ such as an intestine or an artery in order to reach an underlying organ.

Accordingly, it is to be understood that the drawings and descriptions herein are proffered by way of example to facilitate comprehension of the invention and should not be construed to limit the scope thereof.

What is claimed is:

1. A surgical method comprising the steps of:
    inserting a distal end of an elongate tubular member into a patient's abdomen;
    ejecting from a distal end of said tubular member a pair of prongs;
    during said step of ejecting, spreading said prongs apart from one another to form a pair of jaws;
    moving said jaws towards a colon of the patient to insert a portion of said colon between said jaws so that said jaws essentially surround said colon;
    shifting said tubular member towards said prongs, thereby at least partially closing said jaws about said colon to essentially clamp said colon between said jaws, thereby closing said colon at said jaws.

2. The method defined in claim 1 wherein said prongs are connected to an elongate rod member slidably inserted into said tubular member, said step of ejecting including the step of pushing said rod member in a distal direction through said tubular member.

3. The method defined in claim 2 wherein said prongs are integral with one another and made of a resilient material having a limited degree of flexibility, whereby said prongs may be collapsed towards one another by being drawn into said distal end of said tubular member, said step of spreading including the step of automatically spreading said prongs under the action of internal stresses.

4. The method defined in claim 1 wherein said step of inserting includes the step of inserting said tubular member through a trocar sleeve into the patient's abdomen, said method being part of a laparoscopic procedure.

5. The method defined in claim 1, further comprising the step of displacing said colon relative to other organic tissues of the patient by exerting a force on said tubular member and said jaws upon completion of said step of closing.

6. A surgical method comprising the steps of:
    inserting a distal end of an elongate member into a patient's abdomen;
    upon said step of inserting, opening a pair of opposed arcuate arms of a C-shaped clamping member connected to said elongate member at a distal end thereof, thereby forming a pair of jaws;
    moving said jaws towards a colon of the patient to insert a portion of said colon between said jaws so that said jaws essentially surround said colon;
    pressing said arms towards one another to partially flatten said arms, thereby closing said clamping member about said colon to seal said colon; and
    repairing a perforation in said colon while said colon is clamped by said jaws.

7. The method defined in claim 6 wherein said step of inserting includes the step of inserting said elongate member through a trocar sleeve into the patient's abdomen, said method being part of a laparoscopic procedure.

8. The method defined in claim 6, further comprising the step of displacing said organ relative to other organic tissues of the patient by exerting a force on said elongate member and said jaws.

9. A surgical method comprising the steps of:
    providing two elongate members each having a pair of prongs and means operatively connected to the respective prongs for alternatively opening and closing the prongs;
    inserting the distal ends of the two elongate members into a patient's abdomen;
    upon insertion of the distal ends of the two elongate tubular members into a patient's abdomen, opening the prongs to form two pairs of jaws;

moving said pairs of jaws towards a colon having a perforation to insert a portion of said colon between each of said pairs of jaws such that said jaws are located on opposite sides of said perforation;

at least partially closing said pairs of jaws about the colon to clamp the colon on opposite sides of the perforation; and repairing the perforation while the colon is clamped by said jaws.

10. The method defined in claim 11 wherein said elongate members are tubular members, further comprising the step of ejecting the prongs from the distal ends of the respective tubular members upon insertion f the distal ends of the tubular members into the patient's abdomen, said step of opening being executed upon said step of ejecting.

11. The method defined in claim 10 wherein said pairs of prongs are each connected to a respective elongate rod member slidably inserted into the respective tubular member, said step of ejecting including the step of pushing said rod member in a distal direction through said respective tubular member.

12. The method defined in claim 11 wherein said step of closing includes the step of moving said tubular members relative to respective ones of said pairs of jaws, thereby drawing said prongs into the distal ends of said tubular members.

13. The method defined in claim 9 wherein said step of inserting includes the step of inserting said tubular members through trocar sleeves into the patient's abdomen, said method being part of a laparoscopic procedure.

* * * * *

UNITED STATES PATENT AND TRADEMARK OFFICE
CERTIFICATE OF CORRECTION

PATENT NO. : 5,284,162
DATED : February 8, 1994
INVENTOR(S) : Wilk

It is certified that error appears in the above-indentified patent and that said Letters Patent is hereby corrected as shown below:

Column 7

Claim 10, line 1, change "claim 11" to --claim 9--,
line 4, change "f" to --of--.

Signed and Sealed this

Sixteenth Day of August, 1994

Attest:

BRUCE LEHMAN

Attesting Officer     Commissioner of Patents and Trademarks